US005648341A

United States Patent [19]
Sollevi

[11] Patent Number: 5,648,341
[45] Date of Patent: Jul. 15, 1997

[54] METHOD OF TREATING PULMONARY INFLAMMATION BY CONTINUOUS ADMINISTRATION OF AN ADENOSINE-CONTAINING SOLUTION

[75] Inventor: Alf Sollevi, Bromma, Sweden

[73] Assignee: Item Development AB, Stocksund, Sweden

[21] Appl. No.: 144,803

[22] Filed: Oct. 28, 1993

[30] Foreign Application Priority Data

Apr. 21, 1993 [SE] Sweden .................................. 9301324

[51] Int. Cl.$^6$ ...................................................... A61K 31/70
[52] U.S. Cl. ............................................. 514/46; 536/27.6
[58] Field of Search ............................. 514/46; 536/27.6

[56] References Cited

U.S. PATENT DOCUMENTS 5,104,859  4/1992  Sollevi ...................................... 514/46
5,231,086  7/1993  Sollevi ...................................... 514/46

OTHER PUBLICATIONS

Drury et al., "The Physiological Activity of Adenine Compounds with Especial Reference to Their Action Upon the Mammalian Heart," *J. Physiology (Cambridge)*, 68, 213–237 (1929).
Kassell et al., "Cerebral and Systemic Circulatory Effects of Arterial Hypotension Induced by Adenosine," *Neurosurgery*, 58(1), 69–76 (1983).
Fukunaga et al.(I), "ATP–Induced Hypotensive Anesthesia During Surgery," *Anesthesiology*, 57(3), A65 (1982).
Fukunaga et al.(II), "Hypotensive Effects of Adenosine and Adenosine Triphosphate Compared with Sodium Nitroprusside," *Anesthesia and Analgesia*, 61(3), 273–278 (1982).
Kikugawa et al., "Platelet Aggregation Inhibitors. 4. $N^6$–Substituted Adenosines," *J. Medicinal Chem.*, 16(4), 358–364 (1973).
Masters et al., "Platelet Anti–aggregating and Hemodynamic Effects of Adenosine and Prostaglandin $E_1$", *Thorac. Cardiovasc. Surgeon*, 30, 14–20 (1982).
Belardinelli et al, "The cardiac effect of adenosine," Prog. Cardio Dis 1989; 32(1): 73–97.
Ward et al, "Functional consequences of interactions between human neutrophils and ATP, ATPS, and Adenosine," Ann NY Acad Sci 1990; 603: 108–19.
Cronstein et al, "Engagement of Adenosine Receptors Inhibits Hydrogen Peroxide ($H_2O_2$) . . . ," Clinical Immunology and Immunopathology 1987; 42: 76–85.
Cronstein et al, "Adenosine: an endogenous inhibitor of neutrophil–mediated injury to endothelial cells," J Clin Invest 1986; 78: 760–770.

Sollevi, A., "Clinical studies on the effect of adenosine," Elsevier Sci Publ BV. Role of adenosine nucleotides in the biological system. Shoichi Imai, Mikio Nakazawa eds. 1991; pp. 525–537.
Kaminski et al, "Actions of Adenosine on Nitro Blue Tetrazolium Deposition . . . ," Circulation Research 1990; 66(6): 1713–1719.
Ely et al, "Protective effects of adenosine in myocardial ischemia," Circulation 1992; 85(3): 893–904.
Chrisots J. Pitarys II et al, "Reduction of myocardial reperfusion injury by intravenous adenosine administered during the early reperfusion period," Circulation 1991; 83: 237–247.
Tadokoro et al, "Profound infarct size reduction with retrograde coronary venous administration of adenosine," Circulation. Suppl. Nov. 1990.
Boehm et al, "Adenosine cardioplegia: Reducing reperfusion injury of the ischaemic myocardium," Eur J Cardio–thorac Surg 1991; 5: 542–545.
Norton et al, "The effect of intravenous infusions of selective adenosine $A_1$–receptor and $A_2$–receptor agonists on myocardial reperfusion injury," American Heart J 1992; 123: 332–338.
Karasawa et al, "Effect of adenosine, and adenosine $A_1$–antagonist, and their combination in splanchnic occlusion shock in rats," Circulatory Shock 1992; 36: 154–161.
Bileviciute et al, "Neurokinin A is released by capsaicine from rat knee joint afferents if preceded by adenosine or morphine," 7th World Congress on Pain, Paris, Aug. 1993.
Broe et al, "Aspiration pneumonia: Treatment with pulmonary vasodilators," Surgery 1983; 94: 95–99.
Gabridge et al, "Role of Adenine in the Pathogenesis of Mycoplasma pneumoniae infections of Tracheal Epithelium," Med. Microbiol. Immunol. 1978; 165: 43–45.
Bradley et al, "Adenosine prevents phorbol ester injury in rabbit lungs: role of leukotrienes and TNF," Journal of Applied Physiology 1991; 71: 1949–1955.
Pelleg et al, "The Pharmacology of Adenosine," Pharmacotherapy 1990; 10(3): 154–174.

Primary Examiner—John Kight
Assistant Examiner—L. Eric Crane
Attorney, Agent, or Firm—White and Case

[57]  ABSTRACT

The described invention relates to a method of treatment of a pulmonary inflammatory reaction brought about by e.g. bacteraemia, physical trauma or viral infection, with activation of polymorphonuclear white blood cells, said method comprising continuous intravenous infusion of adenosine at a rate effective for such treatment, preferably 2 to 50 µg/ml/min, more preferably 5–20 µg/kg/min in a central vein.

6 Claims, No Drawings

METHOD OF TREATING PULMONARY INFLAMMATION BY CONTINUOUS ADMINISTRATION OF AN ADENOSINE-CONTAINING SOLUTION

DESCRIPTION

1. Field of the Invention

The present invention relates to a method of treatment of a pulmonary inflammatory reaction with activation of polymorphonuclear white blood cells in a human patient. The invention further relates to use of adenosine for the manufacture of a medicament for such treatment and a dosage unit of such medicament.

An object of the invention is to provide effective prophylactic and/or curative pharmacological treatment of a pulmonary inflammatory reaction, for the prevention of pulmonary damage in human subjects. A further object is to provide such treatment for patients in critical conditions, such as patients suffering from bacteraemia, physical trauma or viral infection.

2. Background

Patients in critical conditions, e.g. having various forms of severe infections with bacteraemia (sepsis) as well as haemodynamic instability, often require respiratory support, pharmacologic inotropic treatment, and antibiotics. The condition is associated with high mortality (~30%), and often there are inflammatory reactions in the lungs that may lead to severe impairment, so called "adult respiratory distress syndrome" (ARDS). There may also be damage to other vital organs. When there is multiple organ failure, the mortality is as high as 70–80%. There is an important clinical value to be able to antagonize the body inflammatory reaction that often occurs in the pulmonary tissue as a consequence of sepsis or other critical conditions, thereby preventing respiratory insufficiency. If this can be achieved, catabolism and multi-organ failure can be minimized.

Adenosine is an endogenous nucleoside present in all cell types of the body. It is endogenously formed and released into the extracellular space under physiological and pathophysiological conditions characterized by an increased oxygen demand/supply ratio. This means that the formation of adenosine is accelerated in conditions with increased high energy phosphate degradation. The biological actions of adenosine are mediated through specific adenosine receptors located on the cell surface of various cell types (1). $A_2$-adenosine receptors are activated to induce vasodilation, platelet antiaggregation, and anti-inflammatory actions through polymorphonuclear (PMN) cell stabilization. The $A_1$-receptor activation is often linked to inhibitory influence of metabolic processes, and inhibition of ion-channel flux, such as depression of AV-conduction (2–4).

Exogenous adenosine administration has been subject to clinical studies during the last ten years, as a vasodilator and modulator of AV-conduction (2,5). When adenosine is administered as an intravenous injection, the peak concentration is high and may cause a transient (less than 30 s) inhibition of AV-conduction. This is due to an inhibition of potassium flux, which is clinically used to terminate re-entry supra-ventricular tachycardia involving the AV-node, as well as a diagnostic tool for mapping localisation of excessive pathways. As a vasodilator, adenosine has been used for modifying peripheral resistance and thereby inducing controlled hypotension in anaesthesia, or preventing hypertensive reaction during surgery. The potent vasodilatory effect of adenosine, when administered in a peripheral vein at dosages above 80 µg/kg/min, is also applied for performing maximal coronary vasodilation in conjunction with diagnostic test of ischemic heart disease (IHD). The compound is then infused at a dose of about 140 µg/kg/min, when a stress imaging perfusion test is performed. The pharmacological stress test has also been used in IHD-patients in conjunction with echo-cardiography.

When adenosine is infused at considerably lower dose-range (peripheral venous infusion at dose-rates below 50 µg/kg/min, or central venous infusion below 30 µg/kg/min) vascular effects in the arterial section of the circulation are essentially lacking. Vasodilatory effect in the pulmonary circulation can be detected at a central venous dose of 20–30 µg/kg/min. The mechanism for this dose-dependency is explained by the rapid plasma half-life of adenosine in humans, ranging from 1–10 sec (2,5). The theoretical support for an anti-inflammatory effect of adenosine in conjunction with tissue damage is established on the basis of animal experiments. Consequently, various forms of adenosine administration have demonstrated significant reduction of reperfusion injury of the myocardium from different species (7–11). This type of damage is considered to be dominated by an inflammatory reaction, promoting the tissue necrosis. Thus, there is experimental data from different animal models, suggesting that adenosine treatment may reduce ischemic damage, reduce the degree of neutrophil infiltration, reduce capillary plugging and provide endothelial preservation in the myocardium (6).

On the other hand, there are studies that suggest that adenosine may be pro-inflammatory, thereby promoting tissue damage. This is indicated by a study on the ischemic intestine (12), where an adenosine-receptor antagonistic drug did minimize the damage. Further, it has been shown that adenosine administration can promote the release of the pro-inflammatory endogenous compounds tachykinins in rat joints (13). There is therefore experimental data in the prior art suggesting that adenosine exerts both anti- and pro-inflammatory effects on the organs studied.

U.S. Pat. No. 5,104,859 describes continuous administration of adenosine to reduce pulmonary vascular resistance, and further therapeutic applications based on vasodilation with adenosine.

A pulmonary anti-inflammatory effect of adenosine has not been previously described in animal experiments. Nor have such effects been discussed or described in published clinical studies.

DISCLOSURE OF THE INVENTION

The present invention is based on the finding that exogenous adenosine administration has the ability to prevent inflammation of pulmonary tissue in human subjects.

Accordingly, the invention relates to a method of treatment of a pulmonary inflammatory reaction with activation of polymorphonuclear white blood cells in a human patient, said method comprising continuous intravenous infusion of adenosine at a rate effective for such treatment. As used herein, the word "treatment" is used to cover both prophylactic and curative treatment, unless otherwise is apparent from the specific context.

In particular, the invention is related to treatment of an inflammatory reaction brought about by bacteraemia, physical trauma or viral infection.

In a preferred embodiment of the invention adenosine is given at a rate of 2 to 50 µg/kg/min. The infusion dose is below that required for maximal pulmonary vasodilation, and below doses required for vascular effects in other parts of the body. In particular, adenosine will be administered at a dose of 5–20 µg/kg/min, preferably in a central vein, e.g. the superior caval vein, a brachiocephalic vein or a subclavian vein. In the low dose range of adenosine infusion, the compound has the ability to influence PMN-cells, i.e. neutrophils, in the circulation, preventing them from being activated by endothelial damage during sepsis. The infusion is normally given as long as the risk for an inflammatory reaction prevails, e.g. during the period when the patient is septic, usually 24–72 hours.

For the purposes of this invention, adenosine can be administered to the patient in any pharmaceutically acceptable form suitable for use in continuous, intravenous infusion. A preferred form is an aqueous solution of adenosine, and more preferably adenosine in isotonic saline. A concentration of at least 5 mM (or about 1.5 mg/ml) of solution is desired to avoid the need for excessive infusion rates. The concentration can be up to the solubility limit of adenosine (about 20 mM or 5.5 to 6 mg/ml).

When used in accordance with this invention, the unit dosage form of adenosine typically has a volume of 50 to 1000 ml preferably 100 to 250 ml. The adenosine solution should be sterile and free from fungi and bacteria.

Such solutions are prepared by mixing adenosine with the aqueous carrier, e.g. water or an isotonic solution, and other desired ingredients, to achieve a solution having the desired concentration, and thereafter sterilizing the solution.

Continuous infusion can be achieved by any technique known to the art. Because adenosine has such a short plasma half-life and is active at low administration rates, it is desired that the method be one which minimizes or avoids fluctuations of serum adenosine levels. Accordingly, use of high precision pumps is preferred.

EXAMPLES OF TREATMENT

Example 1

A 67 year old woman with congestive heart disease was acutely operated due to perforated intestine and peritonitis, sepsis and circulatory chock. The patient required large doses of inotropic pharmacological support (adrenaline, noradrenaline, dopamine), respiratory support in a respirator, and received combinations of antibiotics. In the postoperative period the patient was given adenosine (vena cava superior 20 µg/kg/min) for 48 hours. After 24 hours the patient no longer required inotropic support and was spontaneously ventilating without respiratory support after 48 hours. The patient did not develop any pulmonary inflammatory signs on X-ray examinations and was discharged from the ICU (intensive care unit) after four days.

Example 2

A 65 year old woman with a history of alcohol abuse was acutely operated in chock due to peritonitis due to perforation of the colon. The patient was in extremely bad circulatory condition during the first postoperative hours, in spite of massive doses of inotropic support (adrenaline, dobutamine, noradrenaline, and dopamine), ventilated in respirator, and received combinations of antibiotics. The patient received adenosine infusion 12 hours after admission to surgery (vena cava superior 10 µg/kg/min), and adenosine infusion was continued for 72 hours. The circulatory support was eliminated within 24 hours, and the patient was free from respiratory support within 3 days. There were no inflammatory signs on pulmonary X-ray examinations. She was discharged from the ICU five days after admission.

Example 3

A 48 year old man with a post-cholecystectomy bile peritonitis was operated in a septic state, whereby a large bile leakage was found. During cleaning of the abdominal cavity, there was a marked deterioration of the pulmonary function, probably as a result of bacteraemia from the operating area. The patient was given adenosine infusion (10 µg/kg/min in the vena cava superior) dopamine, and a combination of antibiotics The adenosine treatment was continued for 48 hours. Within 24 hours the oxygen concentration in the respirator ventilation was reduced from 80 to 35%, and the patient was free from respiratory support four days after admission to 5 ICU. Pulmonary X-ray did not indicate any pulmonary inflammatory reactions.

BIBLIOGRAPHY

1. Daly, J. W., Adenosine receptors in the central nervous system: Structure-activity relationships for agonists and antagonism. In: Stone, T. W. ed. Purines: Pharmacological and physiological roles, London: Macmillan, 1985: 5–15.

2. Belardinelli, L., Linden, J., Berne, R., The cardiac effects of adenosine. Prog. Cardio Dis 1989: 32:73.

3. Ward, P., Blair, A., Walker, M. and Hagenlocker, B. E., Functional consequences of interactions between human neutrophils and ATP, ATPγS, and Adenosine. Ann NY Acad Sci 1990; 603:108–19.

4a. Cronstein, B. N., Kramer, S. B., Weissmann, G. et al. Adenosine: a physiological modulator of superoxide anion generation by human neutrophils. J Exp Med 1983; 158:1160–1177.

4b. Cronstein, B. N., Levin, R. L, Belanoff, J. et al., Adenosine: an endogenous inhibitor of neutrophil-mediated injury to endothelial cells. J Clin Invest 1986; 78:760–770.

5. Sollevi, A., Clinical studies on the effect of adenosine. Elsevier Sci Publ VB. Role of adenosine nucleotides in the biological system. Shoichi Imai, Mikio Nakazawa eds. 1991: pp 525–537.

6. Ely, S. W., Berne, R. M., Protective effects of adenosine in myocardial ischemia. Circulation, 1992: 893–904.

7. Christos, J., Pitarys, I. I., Virmani, R., Vildibill, J. H. D, Jackson, E. K., Forman M. B., Reduction of myocardial reperfusion injury by intravenous adenosine administered during the early reperfusion period. Circulation 1991; 83:237–247.

8. Tadkoro, H., Kaobyashi, S., Corday, E., Profound infarct size reduction with retrograde coronary venous administration of adenosine. Circulation. Suppl, Nov 1990.

9. Boehm, D. H., Human P. A., von Oppell, U., Owen P., Reichenspurner, H., Opie, L. H., Rose, A. G. and Reichart, B., Adenosine cardioplegia: Reducing reperfusion injury of the ischaemic myocardium. Eur J Cardio-thorac Surg (1991) 5:542–545.

10. Norton, E. D., Jackson, E. K., Turner, M. B., Virmani, R., Forman, M. B., The effect of intravenous infusions of selective adenosine $A_1$-receptor and $A_2$-receptor agonists on myocardial reperfusion injury. A M Heart J 1992; 123:332.

11. Ely, S. W. Berne, R. M., Protective effects of adenosine in myocardial ischemia. Circulation, 85, 893–904, 1992.

12. Karasawa, A., Rochester, J. A., Lefer, A. M., Effects of adenosine, and adenosine $A_1$-antagonist, and their combination in splanchnic occlusion shock in rats. Circulatory Shock, 36, 154–161, 1992.

13. Bileviciute, I., Ekblom, A., Lundeberg, T., Sollevi, A., Theodorsson, E., Neurokinin A is released by capsaicine from rat knee joint afferents if preceded by adenosine or morphine. 7th World Congress on Pain, Paris, Aug. 1993.

I claim:

1. A method for treating a pulmonary inflammatory reaction associated with activation of polymorphonuclear white blood cells in a human patient, comprising the continuous intravenous infusion of adenosine at a rate of 2–50 µg/kg/min.

2. A method as claimed in claim 1, comprising treatment of an inflammatory reaction brought about by bacteraemia.

3. A method as claimed in claim 1, comprising treatment of an inflammatory reaction brought about by a physical trauma.

4. A method as claimed in claim 1, comprising treatment of an inflammatory reaction brought about by a viral infection.

5. A method according to claim 1, wherein the adenosine is administered by intravenous infusion into a central vein of the human at a rate of 5–20 µg/kg/min.

6. A method according to claim 1, wherein the adenosine is administered by intravenous infusion into a central vein of the human at a rate of less than 30 µg/kg/min.

* * * * *